US009290702B2

(12) United States Patent
Lacheen

(10) Patent No.: US 9,290,702 B2
(45) Date of Patent: Mar. 22, 2016

(54) METHODS FOR MONITORING IONIC LIQUIDS USING VIBRATIONAL SPECTROSCOPY

(75) Inventor: Howard Steven Lacheen, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 966 days.

(21) Appl. No.: 13/108,607

(22) Filed: May 16, 2011

(65) Prior Publication Data

US 2012/0296145 A1    Nov. 22, 2012

(51) Int. Cl.
| | |
|---|---|
| *C07C 2/02* | (2006.01) |
| *G01N 21/00* | (2006.01) |
| *G01N 33/00* | (2006.01) |
| *C10G 29/06* | (2006.01) |
| *B01J 19/00* | (2006.01) |
| *G01N 21/3577* | (2014.01) |
| *G01N 21/85* | (2006.01) |
| *B01J 31/02* | (2006.01) |
| *B01J 31/40* | (2006.01) |

(52) U.S. Cl.
CPC .............. *C10G 29/06* (2013.01); *B01J 19/0033* (2013.01); *B01J 31/0284* (2013.01); *B01J 31/0298* (2013.01); *B01J 31/4015* (2013.01); *G01N 21/3577* (2013.01); *G01N 21/85* (2013.01); *B01J 2219/00047* (2013.01); *B01J 2219/00198* (2013.01); *B01J 2219/00227* (2013.01); *C10G 2300/70* (2013.01); *Y10T 436/145555* (2015.01); *Y10T 436/147777* (2015.01)

(58) Field of Classification Search
CPC .......... C07C 2/26; C07C 2/60; B01J 19/0033; B01J 2219/00047; C10G 29/06

USPC ................ 436/37, 96, 98, 171; 585/501, 701
See application file for complete search history.

(56) References Cited

U.S. PATENT DOCUMENTS

| | | | | |
|---|---|---|---|---|
| 5,237,122 | A * | 8/1993 | Eastman et al. | 585/709 |
| 5,382,746 | A * | 1/1995 | Child | C01B 7/195 585/723 |
| 5,407,830 | A * | 4/1995 | Altman et al. | 436/55 |
| 5,681,749 | A * | 10/1997 | Ramamoorthy | G01N 21/359 436/150 |
| 6,096,553 | A * | 8/2000 | Heald | G01N 21/359 250/339.12 |
| 7,531,707 | B2 | 5/2009 | Harris et al. | |
| 7,569,740 | B2 | 8/2009 | Elomari | |
| 7,674,739 | B2 | 3/2010 | Elomari et al. | |
| 7,732,654 | B2 | 6/2010 | Elomari | |
| 2007/0249485 | A1* | 10/2007 | Elomari et al. | 502/20 |
| 2010/0065476 | A1* | 3/2010 | Hommeltoft et al. | 208/108 |
| 2010/0129921 | A1 | 5/2010 | Timken et al. | |

OTHER PUBLICATIONS

Yoo, et al., "Ionic Liquid-Catalyzed Alkylation of Isobutane with 2-Butene" in Journal of Catalysis, 222 (2004) 511-519—month unknown.*

* cited by examiner

*Primary Examiner* — In Suk Bullock
*Assistant Examiner* — Ali Z Fadhel

(57) ABSTRACT

Methods for monitoring ionic liquids using vibrational spectroscopy may involve contacting an infrared (IR) transmissive medium with the ionic liquid, recording an IR spectrum of the ionic liquid, and quantifying at least one chemical characteristic of the ionic liquid based on the IR spectrum. The IR spectrum may be recorded ex situ or in situ. Methods for controlling ionic liquid catalyzed processes are also disclosed, wherein a condition of the ionic liquid may be determined during such processes based on IR spectral analysis of the ionic liquid.

16 Claims, 2 Drawing Sheets

METHODS FOR MONITORING IONIC LIQUIDS USING VIBRATIONAL SPECTROSCOPY

TECHNICAL FIELD

The instant invention relates to monitoring ionic liquids using vibrational spectroscopy.

BACKGROUND

Ionic liquids are salts with melting points lower than 100° C. They may be used in a range of applications, including various chemical reactions, solvent processes, and electrochemistry. The use of ionic liquids as alkylation catalysts has attracted considerable attention in the field of petroleum refining.

Heretofore, several costly and time consuming wet chemical analyses were required in order to determine the composition of both fresh and used ionic liquids. Such tests are destructive and consume valuable ionic liquids, as well as having significant preparation time due to the number of tests performed and the sensitivity of the materials to ambient air.

Vibrational spectra of pure aluminum chloride-butylpyridinium chloride (bupyCl) melts having different $AlCl_3$/bupyCl molar ratios are described by Gale et al. (*Inorg. Chem.* 1980, 19, 2240-2242). Subsequently, Tait et al. performed an IR study of ambient temperature chloroaluminates as a function of melt acidity; in the case of 1-methyl-3-ethylimidazolium chloride/aluminum chloride, results on the effects of adding water to acidic and basic melts were reported (*Inorg. Chem.* 1984, 23, 4352-4360). In both the above studies, vibrational modes were assigned to the corresponding molecular vibration but no attempt was made to develop correlations between signal intensity and melt concentration with respect to pyridinium salt, aluminum chloride or impurities. A method for monitoring ionic liquid catalyst deactivation by titrating hydrolyzed ionic liquid catalyst samples with a basic reagent was described in U.S. Patent Application Publication No. 20100129921 (Timken et al.), the disclosure of which is incorporated by reference herein in its entirety.

As noted above, sample preparation for wet chemistry analyses is both time consuming and may consume significant quantities of the ionic liquid. Accordingly, there is a need for a non-destructive, convenient, and efficient method for monitoring the composition of an ionic liquid before or during an ionic liquid catalyzed process.

SUMMARY

Due to possible variation in the composition and catalytic activity of ionic liquids, it may be valuable to monitor the catalytic activity of an ionic liquid catalyst during or prior to a process using the ionic liquid catalyst. For example, during chloroaluminate ionic liquid catalyzed hydrocarbon conversion reactions, byproduct hydrocarbons known as conjunct polymer react with and deactivate the ionic liquid. Accordingly, in an embodiment of the instant invention the catalytic activity of the ionic liquid may be monitored in order to facilitate the control of ionic liquid catalyzed processes.

According to an aspect of the instant invention, there is provided a method for quantifying one or more chemical characteristics of a fresh, used, or regenerated ionic liquid catalyst before or during an ionic liquid catalyzed process, wherein the method can rapidly provide quantitative data for a range of analytes from a single test with little or no sample preparation. In an embodiment, analysis of ionic liquid may be performed online during ionic liquid catalyzed processes, thereby eliminating the need for sampling per se.

According to one embodiment of the instant invention, a method for assessing the purity of a batch of an ionic liquid comprises contacting an infrared (IR) transmissive medium with the ionic liquid, recording an IR spectrum of the ionic liquid, and determining a purity level of the ionic liquid based on the IR spectrum.

In another embodiment, there is provided a method for monitoring an ionic liquid, the method comprising contacting an IR transmissive medium with the ionic liquid, recording an IR spectrum of the ionic liquid, and quantifying at least one chemical characteristic of the ionic liquid based on the IR spectrum.

In a further embodiment, a method for controlling an ionic liquid catalyzed process comprises recording IR spectral data of the ionic liquid during the process, and determining a condition of the ionic liquid, during the process, based on the IR spectral data.

In yet another embodiment, the invention provides an ionic liquid catalyzed hydrocarbon conversion process comprising contacting a hydrocarbon feed with fresh ionic liquid in a hydrocarbon conversion zone under hydrocarbon conversion conditions to provide: i) a hydrocarbon phase, and ii) a catalyst phase comprising used ionic liquid; regenerating at least a portion of the used ionic liquid in a regeneration zone under regeneration conditions to provide regenerated ionic liquid; and recording IR spectral data of at least one of the fresh ionic liquid, the used ionic liquid, and the regenerated ionic liquid, wherein the IR spectral data is recorded in transmission mode or attenuated total reflectance (ATR) mode.

DETAILED DESCRIPTION

Figure 1:
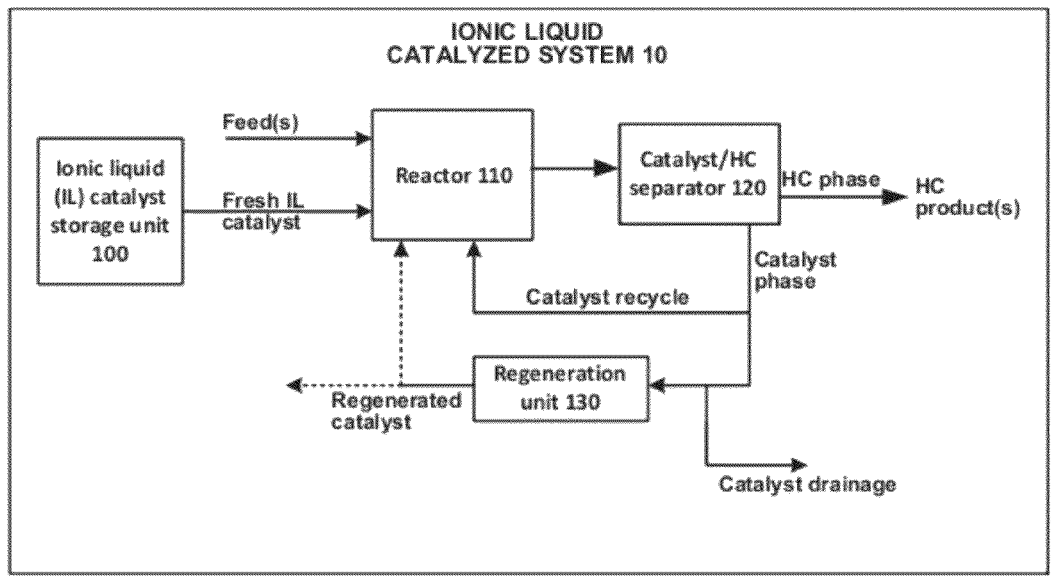
FIG. 1 represents a scheme for an ionic liquid catalyzed process, according to an embodiment of the present invention.

Ionic liquid catalysts are useful for a broad range of processes, including various commercially valuable hydrocarbon conversion processes, such as paraffin alkylation, paraffin isomerization, olefin isomerization, olefin dimerization, olefin oligomerization, olefin polymerization, and aromatic alkylation. The applicant has now discovered that vibrational spectroscopy provides a convenient and efficient method to determine the composition and catalytic activity of ionic liquid catalysts during ionic liquid catalyzed processes. Ionic liquid monitoring according to the instant invention allows for more efficient, steady state operation of such ionic liquid catalyzed processes by maintaining catalytic activity at appropriate levels.

In an embodiment, the invention can be used to monitor and control an ionic liquid catalyzed process, thereby eliminating or greatly reducing the number of wet chemical analyses that might otherwise be necessary. Methods of the invention can be used either ex situ or in situ. In an embodiment, a single test, namely attenuated total reflectance infrared spectroscopy (ATR-IR), may be used to conveniently provide a detailed analysis of the ionic liquid catalyst sufficient to allow process control for steady state operation.

Ionic Liquids

Ionic liquids are generally organic salts with melting points below 100° C. and often below room temperature. They may find applications in various chemical reactions, solvent processes, and electrochemistry. The use of chloroaluminate ionic liquids as alkylation catalysts in petroleum refining has been described, for example, in commonly assigned U.S. Pat. Nos. 7,531,707, 7,569,740, and 7,732,654, the disclosure of each of which is incorporated by reference herein in its entirety.

Most ionic liquids are prepared from organic cations and inorganic or organic anions. Cations include, but are not limited to, ammonium, phosphonium and sulphonium. Anions include, but are not limited to, $BF_4^-$, $PF_6^-$, haloaluminates such as $AlCl_4^-$, $Al_2Cl_7^-$ $AlBr_4^-$, and $Al_2Br_7^-$, $[(CF_3SO_2)_2N]^-$, alkyl sulfates ($RSO_3^-$), and carboxylates ($RCO_2^-$). Ionic liquids for acid catalysis may include those derived from ammonium halides and Lewis acids, such as $AlCl_3$, $TiCl_4$, $SnCl_4$, and $FeCl_3$. Chloroaluminate ionic liquids are perhaps the most commonly used ionic liquid catalyst systems for acid catalyzed reactions.

Examples of chloroaluminate ionic liquid catalysts that may be used in practicing the instant invention include 1-butyl-4-methyl-pyridinium chloroaluminate, 1-butyl-3-methyl-imidazolium chloroaluminate, 1-H-pyridinium chloroaluminate, and N-butylpyridinium chloroaluminate, and mixtures thereof. Methods and processes of the present invention are not limited to any particular ionic liquid(s).

Ionic Liquid Catalyst Degradation and Deactivation

N-butylpyridinium chloroaluminate may be prepared by mixing $AlCl_3$ with butylpyridinium chloride in a molar ratio of approximately 2 to 1. N-butylpyridinium chloroaluminate is an ionic liquid useful as a catalyst in a broad range of hydrocarbon conversion processes. Some possible changes in the composition and catalytic activity of N-butylpyridinium chloroaluminate that may occur during various processes will now be described as examples of ionic liquid catalyst degradation and deactivation, it being understood that the invention is by no means limited to any particular ionic liquid, nor to any particular type of catalyst degradation or deactivation mechanism.

During ionic liquid catalyzed alkylation of isoparaffins with olefins, conjunct polymer may be formed as a byproduct. The conjunct polymer may passivate the ionic liquid catalyst over time resulting in, for example, low octane and high end point alkylate product. The conjunct polymer typically comprises a mixture of hydrocarbons that are highly unsaturated and conjugated molecules containing chloride heteroatoms. The conjunct polymer typically forms stable complexes with ionic liquids, and the conjunct polymer is generally not removed from the ionic liquid catalyst phase by solvent washing or thermal treatments.

Advantageously, the applicant has now discovered that IR spectroscopic analysis may form the basis of a reliable method for quantifying the presence of conjunct polymer in used ionic liquid (see, e.g., Examples 1 and 3).

Monitoring Ionic Liquids

In an embodiment, the instant invention may be used to determine the composition or purity of a sample or batch of manufactured ionic liquid. In another embodiment, the instant invention may be used to determine the composition or purity of an ionic liquid catalyst prior to a process using the ionic liquid catalyst. In yet another embodiment, the instant invention may be used to determine the composition of an ionic liquid, and to monitor the catalytic activity of the ionic liquid catalyst, during a process using the ionic liquid catalyst.

In an embodiment, the instant invention provides a method for monitoring an ionic liquid based on the IR spectrum of the ionic liquid. The IR spectrum may be recorded in transmission mode or in ATR mode. Accordingly, in an embodiment an IR transmissive medium may be contacted with the ionic liquid prior to recording the IR spectrum of the ionic liquid in transmission mode. In another embodiment, an IR transmissive medium may be contacted with the ionic liquid prior to recording the IR spectrum of the ionic liquid in ATR mode. The instant invention is not limited to IR analyses that use transmission and ATR modes.

IR transmissive materials or media that may be used for recording IR spectral data in the transmission mode include but are not limited to silver chloride, zinc selenide, and barium fluoride. IR transmissive media that may be used for recording IR spectral data in ATR mode include thallium bromide-thallium iodide (KRS-5), germanium, diamond, and zinc selenide. In an embodiment, the IR transmissive medium may be disposed within an in-line ATR-IR unit 140 (see, e.g., FIG. 2).

After an IR spectrum of the ionic liquid has been recorded, at least one chemical characteristic or analyte of the ionic liquid may be readily quantified based on the IR spectrum. Such quantification may be provided via Beer's Law relating analyte concentration to absorbance, e.g., over a linear range at a spectral intensity of not more than 1 (one) absorbance unit.

In an embodiment, quantification of the at least one chemical characteristic may be used to determine a purity level of the ionic liquid. In another embodiment, quantification of the at least one chemical characteristic may be used to determine a catalytic activity level of the ionic liquid. In a sub-embodiment, quantification of at least one chemical characteristic may be used as a basis to adjust a rate of ionic liquid catalyst regeneration, or other process condition(s). As a non-limiting example, the at least one chemical characteristic to be quantified may include a conjunct polymer concentration of the ionic liquid.

In an embodiment, methods of the instant invention may be used to monitor the composition, purity level, and/or catalytic activity of the ionic liquid during a process catalyzed by the ionic liquid. In a sub-embodiment, such a process may comprise a hydrocarbon conversion process. In an embodiment, a plurality of IR spectra of the ionic liquid may be recorded during a defined time period, and the IR spectra may be used to quantify and monitor change(s) in at least one chemical characteristic of the ionic liquid during the defined time period. In an embodiment, the defined time period may encompass an entire run of a continuous process, such as an ionic liquid catalyzed hydrocarbon conversion process, or any portion thereof.

In a sub-embodiment, the IR spectrum of the ionic liquid may be continuously recorded, in situ, in ATR mode during an ionic liquid catalyzed process. For example, the IR spectrum may be continuously recorded, in situ, via an in-line ATR-IR unit 140, for example, as described hereinbelow with reference to FIG. 2. In another sub-embodiment, the IR spectrum may be periodically recorded, ex situ, in ATR mode or transmission mode during the process.

Exemplary ionic liquids that may be used in practicing the instant invention may comprise at least one compound of the general formulas A and B:

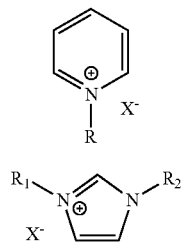

wherein R is selected from the group consisting of H, methyl, ethyl, propyl, butyl, pentyl or hexyl, each of $R_1$ and $R_2$ is selected from the group consisting of H, methyl, ethyl, propyl, butyl, pentyl or hexyl, wherein $R_1$ and $R_2$ may or may not be the same, and X is a chloroaluminate. In a sub-embodiment, an ionic liquid catalyst of the present invention may comprise N-butylpyridinium chloroaluminate. The instant invention is not limited to any particular ionic liquids.

Controlling Ionic Liquid Catalyzed Processes

In an embodiment, the instant invention may be used to control various ionic liquid catalyzed processes. In a sub-embodiment, such ionic liquid catalyzed processes may include hydrocarbon conversion processes. In another sub-embodiment, the instant invention may be used to control an isoparaffin/olefin alkylation process, wherein the ionic liquid catalyst for catalyzing the process may comprise a chloroaluminate ionic liquid.

A scheme for an ionic liquid catalyzed process and system is shown in FIG. 1. Ionic liquid catalyzed system 10 may include an ionic liquid catalyst storage unit 100, a reactor 110, a catalyst/hydrocarbon (HO) separator 120, and a catalyst regeneration unit 130. Dry feeds may be introduced into reactor 110 via one or more reactor inlet ports (not shown). Reactor 110 may also be referred to herein as a hydrocarbon conversion zone. Ionic liquid catalyst may be introduced into reactor 110 via a separate inlet port (not shown). The feeds to reactor 110 may further include a catalyst promoter, such as an alkyl halide. Reactor 110 may be vigorously mixed to promote contact between reactant(s) and ionic liquid catalyst. Hydrocarbon conversion conditions of reactor 110 may be adjusted to optimize process performance for a particular process, e.g., in response to real time IR spectroscopic analysis of the ionic liquid catalyst.

As an example only, the reaction conditions for an ionic liquid catalyzed process of the instant invention may generally include a catalyst volume in the reactor in the range from about 5 vol % to 50 vol %, a temperature of from about −10° C. to 100° C., a pressure in the range from about 300 kPa to 2500 kPa, an isoparaffin to olefin molar ratio in the range from about 2 to 15, and a residence time in the range from about 1 min to 1 hour.

Reactor 110 may contain a mixture comprising ionic liquid catalyst and a hydrocarbon phase, wherein the hydrocarbon phase may comprise at least one hydrocarbon product. The ionic liquid catalyst may be separated from the hydrocarbon phase via catalyst/hydrocarbon separator 120, wherein the hydrocarbon and ionic liquid catalyst phases may be allowed to settle under gravity, by using a coalescer, or by a combination thereof. Thereafter, the hydrocarbon phase may be fractionated, e.g., via distillation, for the separation of hydrocarbon product(s).

At least a portion of the ionic liquid phase may be recycled directly to reactor 110. However, with continued operation of system 10, the ionic liquid catalyst may become partially deactivated. In order to maintain catalytic activity of the ionic liquid, a portion of the ionic liquid phase may be fed to regeneration unit 130 for regeneration of the ionic liquid catalyst. Catalyst regeneration unit 130 may also be referred to herein as a catalyst regeneration zone. In an embodiment, conjunct polymer may be released from the ionic liquid during ionic liquid catalyst regeneration, and the free conjunct polymer may be separated from the regenerated ionic liquid catalyst, e.g., in a conjunct polymer extraction unit (not shown).

With further reference to FIG. 1, ionic liquid catalyst storage unit 100 may be disposed upstream from reactor 110. In a sub-embodiment, an in-line ATR-IR unit 140 (FIG. 2) may be disposed downstream from catalyst storage unit 100 and upstream from reactor 110. In an embodiment of the present invention, the catalytic activity of the ionic liquid in reactor 110 may be maintained under steady state conditions, e.g., based on IR spectroscopic monitoring of the ionic liquid catalyst and the adjustment of one or more process parameters according to the IR spectroscopic data.

In an embodiment, system 10 may be used in an ionic liquid catalyzed alkylation process, e.g., for the production of alkylate gasoline, middle distillate fuels, or base oil. Ionic liquid catalyzed alkylation processes are disclosed in commonly assigned U.S. Pat. Nos. 7,531,707, 7,569,740, and 7,732,654, the disclosure of each of which is incorporated by reference herein in its entirety.

In an embodiment of the instant invention, a method for controlling an ionic liquid catalyzed process may involve recording IR spectral data of the ionic liquid during the process. Thereafter, a condition of the ionic liquid may be determined, during the process, based on the IR spectral data. By determining the condition of the ionic liquid during the process, the condition of the ionic liquid can be monitored, and process parameters adjusted accordingly for efficient, steady state process operation.

In an embodiment of the instant invention, a method for controlling an ionic liquid catalyzed process may involve changing at least one process condition based on the IR spectral data recorded for the ionic liquid catalyst during the process. According to various embodiments of the invention, the IR spectral data may be recorded in ATR mode or transmission mode.

In an embodiment, the IR spectral data may be periodically recorded, ex situ, during the process in ATR mode or transmission mode. In ex situ sampling of the ionic liquid, samples of the ionic liquid may be removed or harvested from the ionic liquid during the process.

In another embodiment, the IR spectral data may be continuously recorded in situ, e.g., via one or more in-line ATR-IR units 140 (FIG. 2), during the process. The ATR-IR unit(s) 140 may be disposed at various locations (e.g., strategically located) within ionic liquid catalyzed system 10 (FIG. 1) for the effective monitoring of the ionic liquid catalyst during processes of the instant invention.

Figure 2:
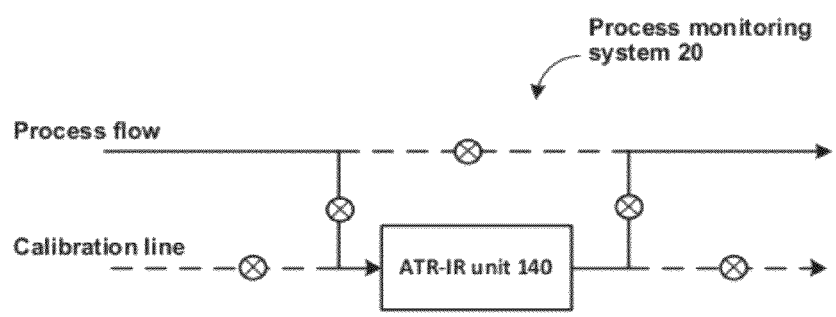
FIG. 2 schematically represents an ionic liquid monitoring system for monitoring an ionic liquid catalyzed process, according to another embodiment of the present invention.

FIG. 2 schematically represents a process monitoring system 20 that may be used in conjunction with system 10 for monitoring the condition of an ionic liquid during an ionic liquid catalyzed process, according to an embodiment of the instant invention. Process monitoring system 20 may include ATR-IR unit 140 for recording IR spectral data of the ionic liquid, wherein ATR-IR unit 140 may be disposed in-line with system 10. In an embodiment, process flow may be diverted via one or more valves to ATR-IR unit 140. Where appropriate, the temperature and/or pressure of process flow may be adjusted prior to contacting an in-line ATR-IR unit 140 with the ionic liquid. In embodiments in which the IR spectral data is recorded in situ, no sampling per se of the ionic liquid is required, i.e., none of the ionic liquid is wasted or consumed as a result of IR spectroscopic monitoring thereof.

With further reference to FIG. 2, process monitoring system 20 may further include a calibration line, which may be controllable via one or more valves, for calibrating ATR-IR unit 140. As an example, ATR-IR unit 140 may be calibrated using a standard ionic liquid, i.e., having a known composition or purity level, such as 100% purity or other known % purity level. In another example, ATR-IR unit 140 may be calibrated using a standard ionic liquid (e.g., fresh N-butylpyridinium chloroaluminate) that has been spiked with a known concentration of conjunct polymer or other analyte.

In an embodiment of the instant invention, IR spectral data recorded for the ionic liquid during a process may be utilized to indicate an amount of conjunct polymer that may have accumulated in the ionic liquid. In another embodiment, the IR spectral data recorded for the ionic liquid catalyst during a hydrocarbon conversion process may be used to indicate a purity level of the ionic liquid and an extent of ionic liquid catalyst deactivation.

Ionic liquid catalyst that contains substantial amounts of conjunct polymer, and/or that has been at least partially deactivated during a hydrocarbon conversion process of the instant invention, may be referred to as used catalyst. With reference to FIG. 1, hydrocarbon conversion processes of the instant invention may include a used catalyst regeneration step performed under catalyst regeneration conditions in catalyst regeneration unit 130 to provide regenerated catalyst. Regenerated catalyst from regeneration unit 130 may have a level of catalytic activity and composition at least substantially similar to those of fresh ionic liquid catalyst. In some instances, e.g., depending on a particular set of regeneration conditions, the regenerated catalyst may contain some small quantities of impurities, such as trace quantities of conjunct polymer. In an embodiment of the instant invention, IR spectral data recorded for the ionic liquid during a hydrocarbon conversion process may be used to indicate an extent of catalyst regeneration.

Typical regeneration conditions for catalyst regeneration unit 130 may include a temperature generally in the range from about −20° C. to 350° C., a pressure typically in the range from about atmospheric to 5000 psig, and a contact time typically in the range from about 0.1 minute to 24 hours. Methods for controlling ionic liquid catalyzed processes according to the instant invention may further include a step of changing at least one of the catalyst regeneration conditions based on the IR spectral data recorded for regenerated catalyst. In an embodiment, the IR spectral data may be recorded by an in-line ATR-IR unit disposed downstream from regeneration unit 130.

Various methods have been described for the regeneration of used ionic liquid catalyst. As an example, a process for the regeneration of ionic liquid catalyst by treatment with a regeneration metal (e.g., Al) is described in commonly assigned U.S. Pat. No. 7,674,739, the disclosure of which is incorporated by reference herein in its entirety.

In another embodiment of the instant invention, IR spectral data for at least one of fresh ionic liquid catalyst, used ionic liquid catalyst, and regenerated ionic liquid catalyst may be recorded both in situ and ex situ during a hydrocarbon conversion process. As an example only, IR spectral data recorded continuously, in situ, during the hydrocarbon conversion process by an in-line ATR-IR unit 140 may be supplemented with IR spectral data recorded periodically, ex situ, during the hydrocarbon conversion process. In the case of ex situ IR analyses, the IR spectral data may be obtained in either transmission mode or ATR mode.

Ionic Liquid Catalyzed Hydrocarbon Conversion Processes

Various ionic liquids may be of value in commercial processes. For example, chloroaluminate ionic liquids may be used to catalyze hydrocarbon conversion processes. Such hydrocarbon conversion processes may comprise a broad range of reactions, including alkylation, polymerization, dimerization, oligomerization, acylation, olefin metathesis, and copolymerization.

In one embodiment, ionic liquid catalyzed hydrocarbon conversion processes of the instant invention may involve contacting one or more hydrocarbon feeds with ionic liquid catalyst in a hydrocarbon conversion zone under hydrocarbon conversion conditions to provide: i) a hydrocarbon phase, and ii) a catalyst phase comprising used ionic liquid. Such hydrocarbon conversion processes may further involve regenerating at least a portion of the used ionic liquid in a regeneration zone under regeneration conditions to provide regenerated ionic liquid. Such hydrocarbon conversion processes may still further involve recording IR spectral data for at least one of the fresh ionic liquid, the used ionic liquid, and the regenerated ionic liquid, wherein the IR spectral data may be used to determine the composition or purity level of the ionic liquid. The IR spectral data may also be used to indicate a catalytic activity of at least one of the fresh ionic liquid, the used ionic liquid, and the regenerated ionic liquid.

In an embodiment, the IR spectral data may be recorded ex situ in ATR mode or transmission mode. In another embodiment, the IR spectral data may be recorded in situ using an in-line ATR-IR unit 140, substantially as described hereinabove with respect to controlling ionic liquid catalyzed processes.

In an embodiment, in situ or ex situ IR spectral analysis of the ionic liquid at various locations of system 10 (FIG. 1) may be used to indicate a concentration of conjunct polymer in at least one of the fresh ionic liquid, the used ionic liquid, and the regenerated ionic liquid.

As non-limiting examples, hydrocarbon conversion processes of the instant invention may comprise alkylation and polymerization reactions, as well as dimerization, oligomerization, acylation, olefin metathesis, and copolymerization. A hydrocarbon feed for such hydrocarbon conversion processes may comprise various streams in a petroleum refinery, a gas-to-liquid conversion plant, or a coal-to-liquid (CTL) conversion plant, including streams from Fischer-Tropsch synthesis units, naphtha crackers, middle distillate crackers or wax crackers, as well as FCC off-gas, FCC light naphtha, coker off-gas, coker naphtha, and the like. Some such streams may contain significant amounts of both isoparaffin(s) and olefin(s). In an embodiment, a hydrocarbon conversion process of the invention may comprise an isoparaffin/olefin alkylation reaction (see, for example, U.S. Pat. No. 7,531,707, the disclosure of which is incorporated by reference herein in its entirety).

In an embodiment, ionic liquids for catalyzing hydrocarbon conversion processes of the instant invention may comprise at least one compound of the general formulas A and B:

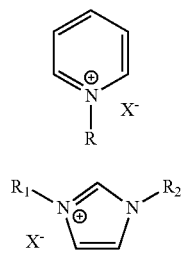

wherein R is selected from the group consisting of H, methyl, ethyl, propyl, butyl, pentyl or hexyl, each of $R_1$ and $R_2$ is selected from the group consisting of H, methyl, ethyl, propyl, butyl, pentyl or hexyl, wherein $R_1$ and $R_2$ may or may not be the same, and X is a chloroaluminate. An exemplary chloroaluminate ionic liquid catalyst that may be useful in hydrocarbon conversion processes of the invention is N-butylpyridinium chloroaluminate.

The following examples illustrate, but do not limit, the present invention.

EXAMPLES

Example 1

Quantification of Conjunct Polymer in Used Catalyst by Transmission FT-IR

IR spectra were separately recorded for fresh N-butylpyridinium chloroaluminate catalyst (0% conjunct polymer), isolated conjunct polymer, and for three samples of used catalyst containing 1.5%, 7.0%, and 16% of conjunct polymer (as quantified by the hydrolysis method of Example 2). The fresh N-butylpyridinium chloroaluminate catalyst was purchased.

IR samples were prepared by placing one drop of ionic liquid between AgCl plates and the liquid was spread into a visually uniform layer. This step was performed in a dry $N_2$ atmosphere to prevent hydrolysis or other contamination of the catalyst samples. After preparing the sample, it was transferred in ambient air to a Varian 7000e FT-IR, and spectra were recorded in transmission mode using 16-32 scans. Spectra were converted to absorbance units for analysis.

The IR spectrum for fresh N-butylpyridinium chloroaluminate catalyst (0% conjunct polymer) contained modes at 1175, 1467, 1490, 1500, 1634 $cm^{-1}$.

Figure 3:
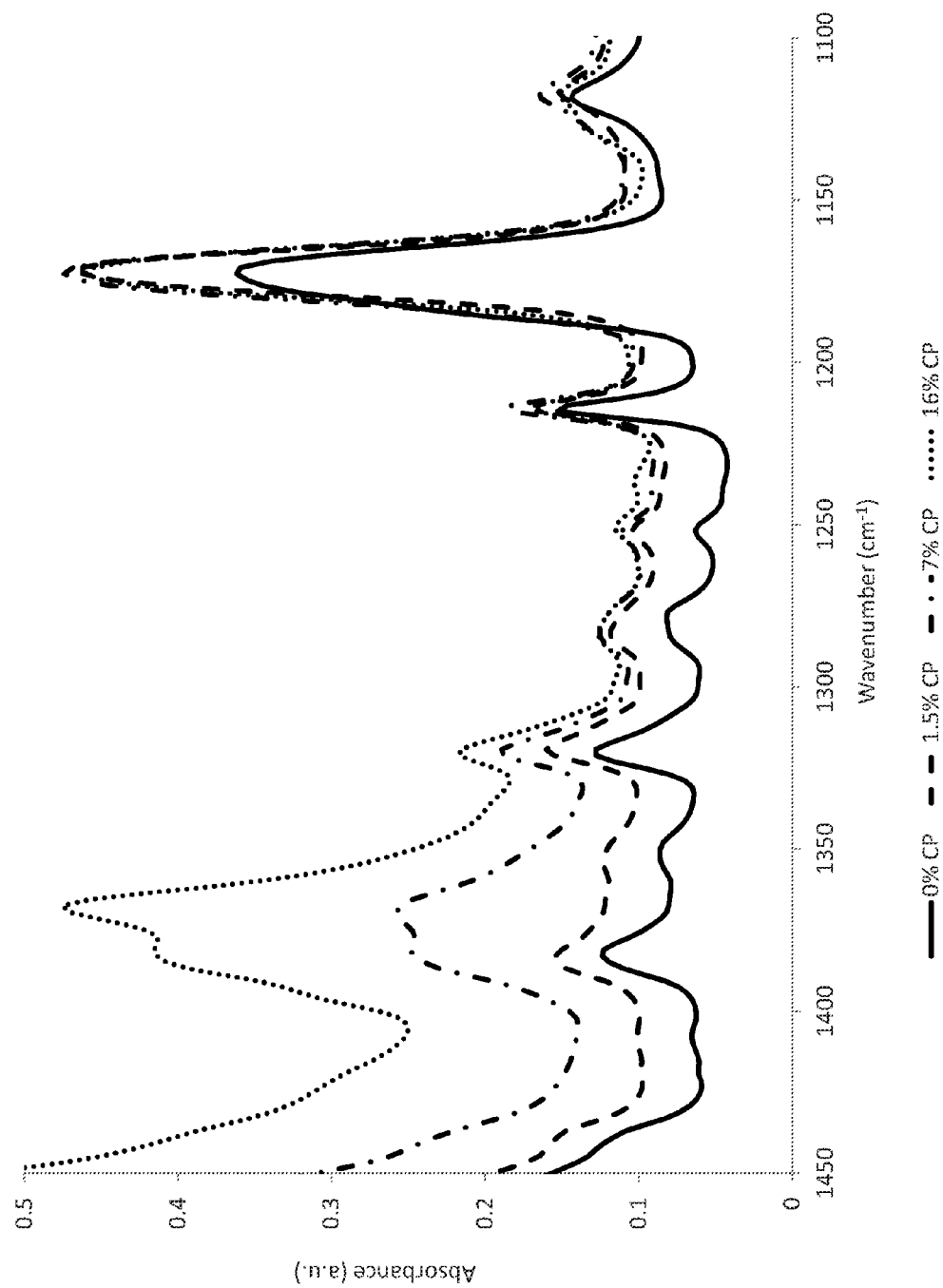
FIG. 3 shows transmission IR spectra for fresh ionic liquid catalyst and for used ionic liquid catalyst containing various amounts of conjunct polymer, according to an aspect of the present invention.

The butylpyridinium chloroaluminate mode at 1175 $cm^{-1}$ was utilized as an internal standard to normalize the spectra (FIG. 3). For the three samples of used catalyst containing 1.5%, 7.0%, and 16% of conjunct polymer, the band attributable to conjunct polymer near 1370 $cm^{-1}$ increased proportionally to the conjunct polymer concentration. The integrated areas of the modes in the same energy range were used to compare the spectra.

The integrated areas for each of regions 1330-1410 cm-1 (A) and 1150-1198 cm-1 (B) for each sample are shown in Table 1, together with the A/B area ratio. The area of the band at 1150-1198 $cm^{-1}$ was used as an internal standard to correct for different sample thicknesses.

TABLE 1

Areas A and B and A:B ratios for ionic liquid samples recorded in transmission IR mode

| Sample (% conjunct polymer measured by hydrolysis) | Area (A)[1] | Area (B)[2] | A/B |
| --- | --- | --- | --- |
| 0% | 1.73 | 7.54 | 0.23 |
| 1.5% | 4.41 | 18.02 | 0.24 |
| 7% | 2.95 | 4.92 | 0.60 |
| 16% | 3.12 | 2.70 | 1.16 |

[1]1330-1410 $cm^{-1}$
[2]1150-1198 $cm^{-1}$

Example 2 (Comparative)

Quantification of Conjunct Polymer in Used Catalyst by Hydrolysis

The concentration of conjunct polymer in samples of used ionic liquid catalyst was performed in a dry $N_2$ atmosphere, as follows. A 20 mL sample of used catalyst was washed with hexanes to remove any soluble hydrocarbon feeds and reaction products; then, residual solvent was removed by vacuum stripping of the catalyst. Then the used catalyst was mixed with water to dissolve the ionic liquid and separate the conjunct polymer, which is insoluble in water. The concentration of conjunct polymer was calculated from the weight of the recovered conjunct polymer and the weight of the used catalyst (after solvent wash and stripping). The conjunct polymer content of three samples of used catalyst was determined to be 1.5%, 7% and 16% by weight.

Example 3

Quantification of Conjunct Polymer in Used Catalyst by ATR FT-IR

IR spectra were recorded in ATR mode using an A2 compact ATR spectrometer (A2 Technologies, Danbury, Conn.) equipped with a diamond window. Spectra were recorded for the same samples as used in Example 1, i.e., fresh N-butylpyridinium chloroaluminate (0% conjunct polymer), conjunct polymer (isolated from used N-butylpyridinium chloroaluminate catalyst), and used N-butylpyridinium chloroaluminate catalyst containing 1.5%, 7%, and 16% conjunct polymer.

In the spectra of used catalyst samples containing 1.5%, 7.0%, and 16% conjunct polymer, the band near 1370 $cm^{-1}$ was observed to increase proportionally to the conjunct polymer concentration. The ratio of integrated areas of modes A and B (defined in Example 1) was used to compare spectra, substantially as described for Example 1. The NB area ratio for each sample is shown in Table 2.

TABLE 2

Area A:B ratio for samples recorded in ATR-IR mode

| Sample (% conjunct polymer measured by hydrolysis) | Area A[1]/ Area B[2] |
| --- | --- |
| 0% | 0.27 |
| 1.5% | 0.27 |
| 7% | 0.63 |
| 16% | 1.1 |

[1]1330-1410 $cm^{-1}$
[2]1150-1198 $cm^{-1}$

The ratios of integrated areas A/B as determined by ATR-IR in Example 2 were broadly similar to those determined by transmission IR (Example 1, Table 1). However, in the case of samples analyzed in ATR mode, the use of an internal standard (as in Example 1) is not required, and the conjunct polymer concentration may be determined based solely on the integrated area of the band near 1370 cm$^{-1}$. A linear correlation can be developed using least squares analysis between the known conjunct polymer amount (as measured by hydrolysis) and the area of the vibrational mode centered at 1370 cm-$^1$. Such correlations were used to calibrate the ATR and transmission spectrometers for conjunct polymer measurements.

Examples 1 and 3 show that the conjunct polymer content of an unknown sample of used ionic liquid catalyst can be quantified by IR analysis in transmission mode or ATR mode.

Although the instant invention has been described in connection with specific embodiments thereof, it will be appreciated by those skilled in the art that additions, deletions, modifications, and substitutions not specifically described may be made without departing from the spirit and scope of the invention as defined in the appended claims.

What is claimed is:

1. A method for monitoring an ionic liquid, wherein the method comprises monitoring the ionic liquid during a hydrocarbon conversion process catalyzed by the ionic liquid wherein a conjunct polymer is formed in the ionic liquid during the hydrocarbon conversion process, comprising:
    contacting an infrared (IR) transmissive medium with the ionic liquid;
    recording an IR spectrum of the ionic liquid; and
    quantitatively determining a concentration of the conjunct polymer in the ionic liquid based on the IR spectrum, using solely an IR band around 1370 cm$^{-1}$.

2. The method according to claim 1, wherein the IR spectrum is continuously recorded, in situ, in attenuated total reflectance (ATR) mode during the hydrocarbon conversion process.

3. The method according to claim 1, wherein the IR spectrum is periodically recorded, ex situ, in ATR mode or transmission mode during the hydrocarbon conversion process.

4. The method according to claim 1, wherein the contacting step comprises contacting the ionic liquid with the IR transmissive medium within an in-line ATR-IR unit during the hydrocarbon conversion process.

5. The method according to claim 1, wherein the ionic liquid comprises N-butylpyridinium chloroaluminate.

6. The method according to claim 1, wherein the determining the amount of the conjunct polymer in the ionic liquid does not use an internal standard.

7. The method of claim 1, wherein the infrared (IR) transmissive medium is selected from the group consisting of silver chloride, zinc selenide, barium fluoride, thallium bromide-thallium iodide, germanium, diamond, and zinc selenide.

8. The method of claim 1, wherein the recording the IR spectrum of the ionic liquid uses an attenuated total reflectance IR unit and the infrared (IR) transmissive medium is selected from the group consisting of thallium bromide-thallium iodide, germanium, diamond, and zinc selenide.

9. A method for controlling an ionic liquid catalyzed hydrocarbon conversion process in which the ionic liquid is at least partially deactivated during the process to form a used catalyst, wherein the process includes regenerating the used catalyst under catalyst regeneration conditions in a catalyst regeneration zone to provide a regenerated catalyst, and an IR spectral data indicates an extent of catalyst regeneration, comprising:
    recording infrared (IR) spectral data of an ionic liquid during the process;
    quantitatively determining an amount of a conjunct polymer in the ionic liquid based on the IR spectral data, using solely an IR band around 1370 cm$^{-1}$; and changing at least one of the catalyst regeneration conditions based on the IR spectral data.

10. The method according to claim 9, wherein the IR spectral data is recorded in ATR mode or transmission mode.

11. The method according to claim 9, wherein the IR spectral data is periodically recorded, ex situ, during the process in attenuated total reflectance (ATR) mode or transmission mode.

12. The method according to claim 9, wherein the IR spectral data is continuously recorded, in situ, by an in-line ATR-IR unit during the process.

13. The method according to claim 9, wherein the process is performed in a reactor, the IR spectral data is recorded by an in-line ATR-IR unit during the process, and the ATR-IR unit is disposed downstream from a catalyst storage unit and upstream from the reactor.

14. The method according to claim 9, wherein the conjunct polymer is formed as a byproduct of the process, the conjunct polymer accumulates in the ionic liquid during the process, and the IR spectral data indicates an amount of the conjunct polymer in the ionic liquid.

15. The method according to claim 9, wherein the determining the amount of the conjunct polymer in the ionic liquid does not use an internal standard.

16. The method of claim 9, wherein the step of recording infrared (IR) spectral data of the ionic liquid uses an attenuated total reflectance IR unit having an infrared (IR) transmissive medium selected from the group consisting of thallium bromide-thallium iodide, germanium, diamond, and zinc selenide.

* * * * *